(12) United States Patent
Kuwada et al.

(10) Patent No.: US 8,986,284 B2
(45) Date of Patent: Mar. 24, 2015

(54) CATHETER

(71) Applicant: Asahi Intecc Co. Ltd., Nagoya-shi, Aichi (JP)

(72) Inventors: Shuichi Kuwada, Seto (JP); Fumiyoshi Oshima, Nagoya (JP); Kazutaka Yamada, Kasugai (JP)

(73) Assignee: Asahi Intecc Co., Ltd., Nagoya-shi (JP)

( * ) Notice: Subject to any disclaimer, the term of this patent is extended or adjusted under 35 U.S.C. 154(b) by 0 days.

(21) Appl. No.: 13/903,463

(22) Filed: May 28, 2013

(65) Prior Publication Data
US 2014/0046301 A1   Feb. 13, 2014

(30) Foreign Application Priority Data
Aug. 7, 2012  (JP) .................................. 2012-174528

(51) Int. Cl.
  *A61M 25/00* (2006.01)
  *B29C 70/22* (2006.01)
  *B29L 31/00* (2006.01)
  *A61M 25/01* (2006.01)

(52) U.S. Cl.
  CPC ......... *A61M 25/005* (2013.01); *A61M 25/0012* (2013.01); *B29C 70/22* (2013.01); *B29L 2031/7542* (2013.01); *A61M 25/0041* (2013.01); *A61M 25/0045* (2013.01); *A61M 25/0054* (2013.01); *A61M 25/0108* (2013.01)
  USPC .......................................... 604/527; 604/524

(58) Field of Classification Search
  CPC .......... A61M 25/0053; A61M 25/005; A61M 25/0045; A61M 25/0012

USPC .......................... 604/527, 524, 526, 528, 529
  See application file for complete search history.

(56) References Cited

U.S. PATENT DOCUMENTS 4,634,042 A * 1/1987 Smith ......................... 228/173.4
4,817,613 A   4/1989 Jaraczewski et al.
(Continued)

FOREIGN PATENT DOCUMENTS

CA   2 358 661 A1   7/2000
CA   2 564 294 A1   7/2000
(Continued)

OTHER PUBLICATIONS

Extended European Search Report issued in European Patent Application No. 13173132.5 dated Dec. 20, 2013.
(Continued)

*Primary Examiner* — Bhisma Mehta
*Assistant Examiner* — Hamza Darb
(74) *Attorney, Agent, or Firm* — Oliff PLC

(57) ABSTRACT

A body of a catheter includes an inner layer, a braid, and an outer layer. The braid includes first and second wires. The first and second wires can be joined together such that the distal end portion of the first wire winds itself around a side surface of the second wire. A joint includes a first joint portion positioned at the intersection point, a second joint portion positioned beyond the first wire in a width direction of the first wire, and a third joint portion positioned beyond the second wire in a width direction of the second wire. Thus, even when the first and second wires have small thicknesses for size reduction of the braid, the first and second wires can be joined together with high joint strength by increasing the area of the second joint portion or the thickness of the third joint portion.

10 Claims, 9 Drawing Sheets

(56) References Cited

U.S. PATENT DOCUMENTS

| | | |
|---|---|---|
| 5,667,499 A | 9/1997 | Welch et al. |
| 6,171,295 B1 | 1/2001 | Garabedian et al. |
| 6,508,805 B1 | 1/2003 | Garabedian et al. |
| 6,562,022 B2 | 5/2003 | Hoste et al. |
| 6,709,429 B1 | 3/2004 | Schaefer et al. |
| 6,866,660 B2 | 3/2005 | Garabedian et al. |
| 6,942,654 B1 | 9/2005 | Schaefer et al. |
| 7,172,617 B2 * | 2/2007 | Colgan et al. ............. 623/1.11 |
| 7,597,830 B2 | 10/2009 | Zhou |
| 7,905,877 B1 | 3/2011 | Jimenez et al. |
| 7,985,214 B2 | 7/2011 | Garabedian et al. |
| 8,366,699 B2 | 2/2013 | Jimenez et al. |
| 8,475,431 B2 | 7/2013 | Howat |
| 2001/0001112 A1 * | 5/2001 | Hayman ..................... 604/21 |
| 2002/0072729 A1 * | 6/2002 | Hoste et al. ................ 604/524 |
| 2003/0009184 A1 * | 1/2003 | Pepin ......................... 606/159 |
| 2004/0162543 A1 | 8/2004 | Schaefer et al. |
| 2005/0010194 A1 | 1/2005 | Zhou |
| 2008/0125752 A1 * | 5/2008 | Gunderson et al. ......... 604/527 |
| 2010/0016837 A1 | 1/2010 | Howat |
| 2012/0109078 A1 * | 5/2012 | Schaeffer .................... 604/264 |
| 2012/0271408 A1 * | 10/2012 | Colgan et al. ............. 623/1.22 |
| 2013/0131641 A1 | 5/2013 | Jimenez et al. |
| 2013/0255062 A1 | 10/2013 | Howat |

FOREIGN PATENT DOCUMENTS

| | | |
|---|---|---|
| CA | 2 660 412 A1 | 2/2008 |
| EP | 0 732 117 A2 | 9/1996 |
| EP | 0 732 117 B1 | 9/1996 |
| EP | 0 732 117 B1 | 8/1999 |
| EP | 2 453 967 B1 | 5/2013 |
| JP | B2-3184086 | 7/2001 |
| JP | A-2005-230318 | 9/2005 |
| JP | A-2006-181258 | 7/2006 |
| WO | WO 00/43061 A1 | 7/2000 |
| WO | WO 2008/019236 A1 | 2/2008 |
| WO | WO 2011/008738 A1 | 1/2011 |

OTHER PUBLICATIONS

Nov. 5, 2014 Notification of Reasons for Refusal issued in Japanese Patent Application No. 2012-174528 with English Translation.

* cited by examiner

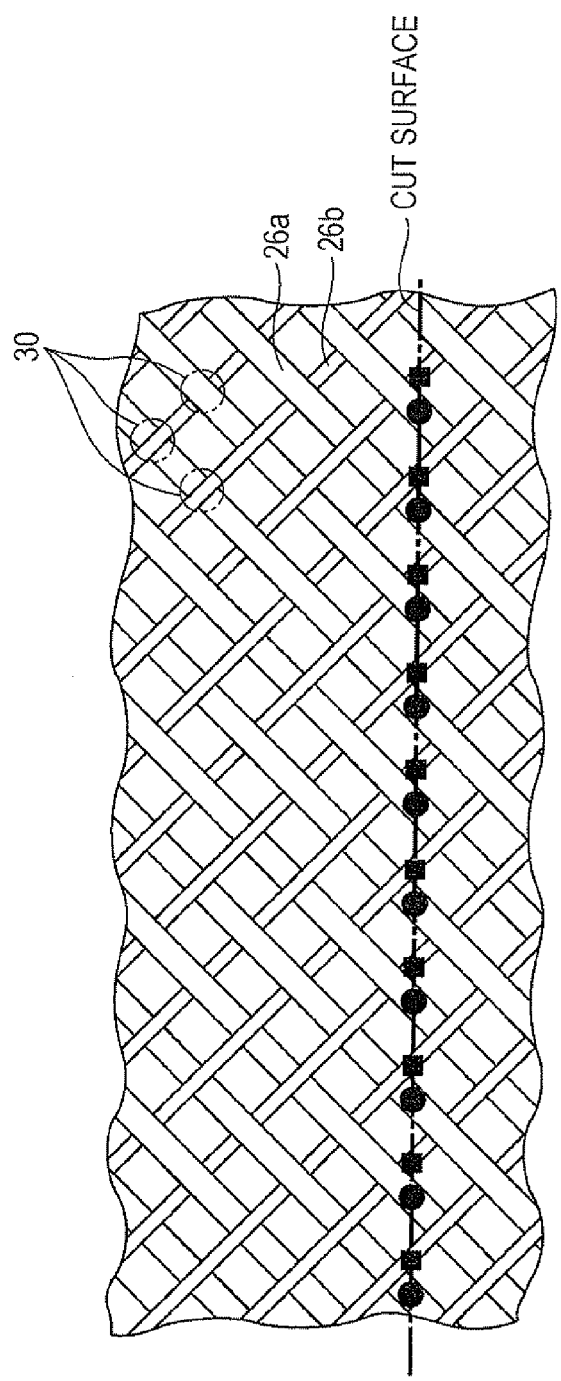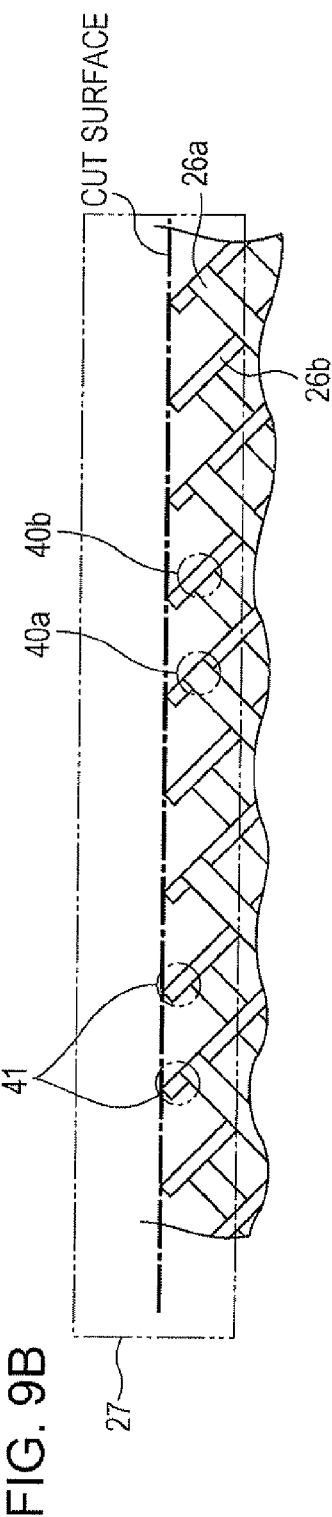
FIG. 9A
FIG. 9B

CATHETER

CROSS-REFERENCE TO RELATED APPLICATION

This application claims priority to Japanese Patent Application No. 2012-174528 filed in the Japan Patent Office on Aug. 7, 2012, the entirety of which is hereby incorporated by reference.

BACKGROUND OF THE INVENTION

1. Field of the Invention

The disclosed embodiments relate to medical devices. More specifically, the disclosed embodiments relate to catheters that are inserted into blood vessels or the like.

2. Description of Related Art

A catheter that is inserted into a tubular organ, such as a blood vessel, an alimentary canal, or a ureter, or an internal bodily tissue, structurally includes an inner layer (base tube) made of a resin, an outer layer surrounding the outer periphery of the inner layer and made of a resin, and a braid (reinforcement layer) interposed between the inner layer and the outer layer. This braid is formed by weaving wires made of a metal such as copper or stainless steel together in consideration of properties required for a catheter, such as pushability, torque transfer capability, and pressure resistance. For example, a braid is known in which first wires made of stainless steel and second wires made of stainless steel are wound such that the first wires form left-handed helices and the second wires form right-handed helices (see Japanese Patent No. 3184086).

In order to prevent woven first wires and second wires from being detached from one another, a braid has been developed in which first wires and second wires are welded or joined together by an adhesive or the like at intersection points at which the first wires and the second wires cross one another (see U.S. Pat. No. 6,562,022, for example). A braid has also been developed in which first wires and second wires are welded by a laser beam at intersection points at which the first wires and the second wires cross one another (see Japanese Unexamined Patent Application Publication No. 2005-230318, for example).

However, with the above described method of joining the first wires and the second wires together at the intersection points, it is difficult to join the first wires and the second wires together with high joint strength. Specifically, a thin braid is required for size reduction of a catheter body. If, however, the thicknesses of first wires and second wires of the braid are reduced for this purpose, a necessary joint strength between the first wires and the second wires is not sufficiently secured by only joining the first wires and the second wires together at the intersection points. If, for securing a necessary joint strength, the first wires and the second wires are joined together by using another member such as a clip or an adhesive, the object of reducing the thickness of the braid will not be achieved.

If, on the other hand, the material used for first wires differs from the material used for second wires, it may be difficult to weld the first wires and the second wires together by a laser beam. In this case, the only method of joining the first wires and the second wires together is to use another member such as a clip or an adhesive, and thus the object of reducing the thickness of the braid will not be achieved.

SUMMARY

Accordingly, the present invention has been developed in view of the above circumstances and provides a catheter including a braid including thin first wires and thin second wires that are joined together with high joint strength.

The following measures are taken to produce the above catheter.

According to an aspect of the present invention, a catheter includes an inner layer made of a resin; a braid surrounding an outer periphery of the inner layer, the braid including a first wire and a second wire; and an outer layer surrounding an outer periphery of the braid, the outer layer being made of a resin. The first wire and the second wire are joined together via a joint at which a distal end portion of the first wire covers a side surface of the second wire.

In the catheter according to the above aspect of the present invention, the distal end portion of the first wire covers the side surface of the second wire at the joint, so that the first wire and the second wire can be joined together without using another member such as a clip or an adhesive. In addition, even when the first wire and the second wire have small thicknesses, the joint strength between the first wire and the second wire can be flexibly changed by adjusting the area of the side surface of the second wire covered by the distal end portion of the first wire.

BRIEF DESCRIPTION OF THE DRAWINGS

FIGS. 9A and 9B are plan views of a distal end portion of a braid according to an embodiment other than that illustrated in FIGS. 4A and 4B.

DETAILED DESCRIPTION OF EMBODIMENTS

Figure 1:
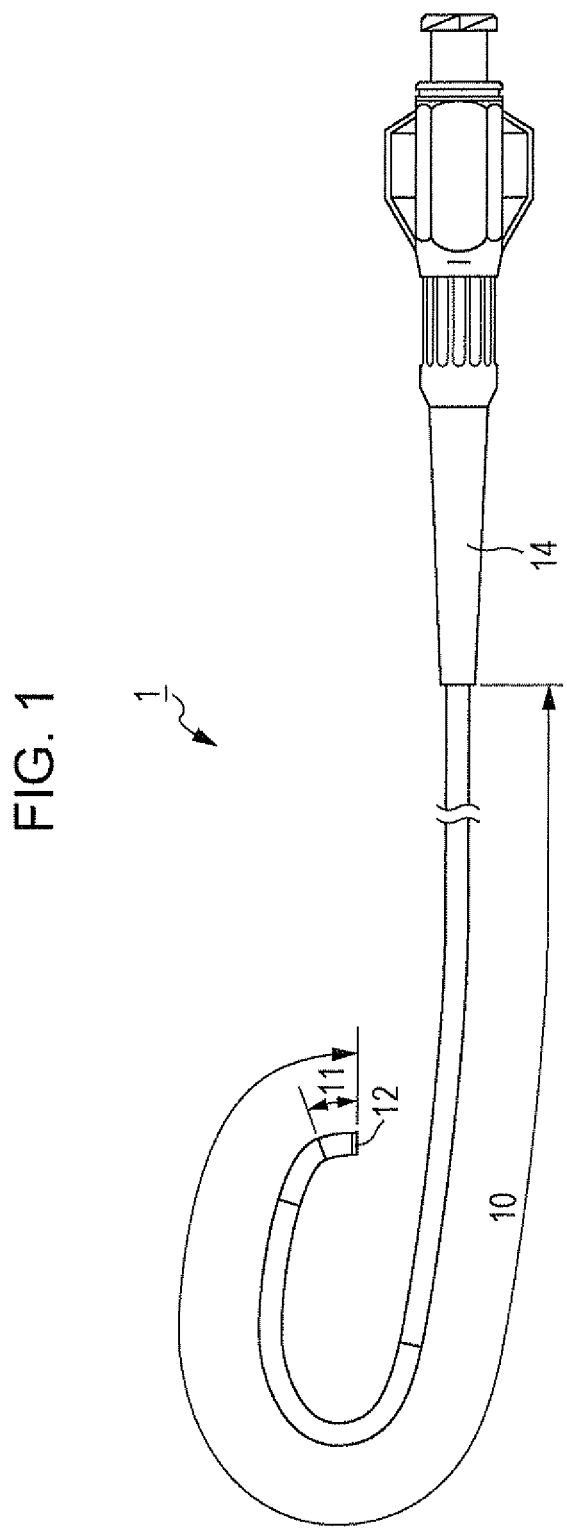
FIG. 1 illustrates the entirety of a catheter according to an embodiment.
Figure 2:
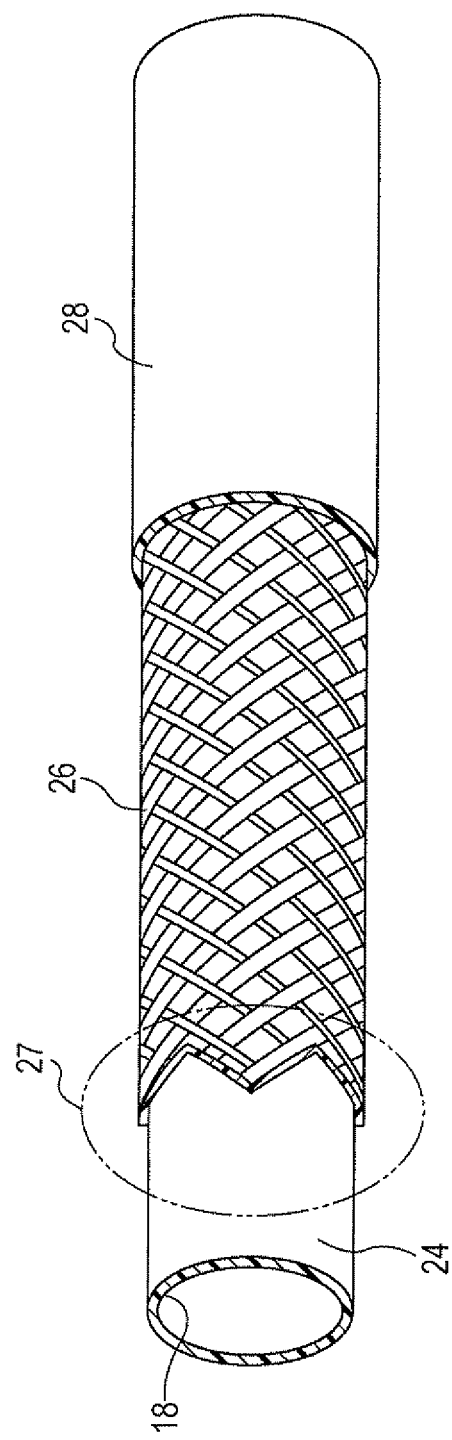
FIG. 2 illustrates a distal end portion of the catheter, from which a distal end tip is excluded for ease of illustration.
Figure 3:
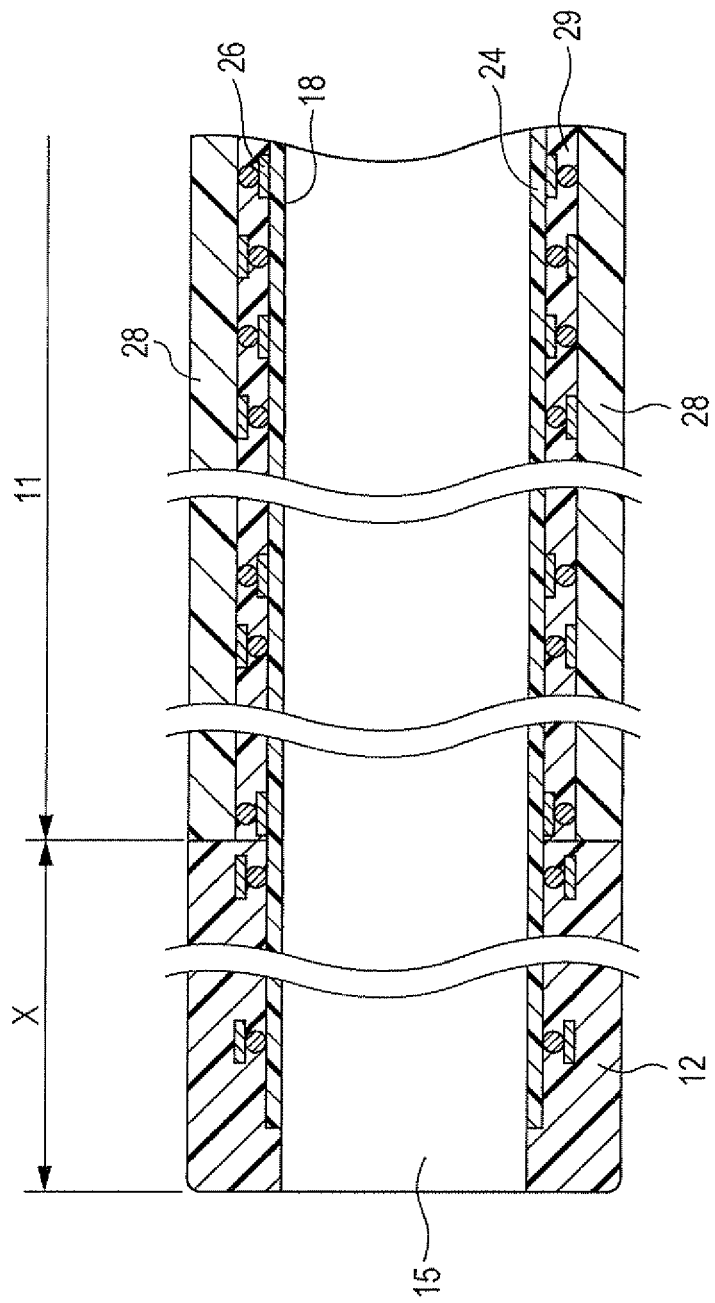
FIG. 3 is a cross-sectional view of the distal end portion and the distal end tip of the catheter.

Referring to FIGS. 1 to 9B, a catheter 1 according to an embodiment will be described as an example. In FIGS. 1, 2, and 3, the left side is a distal side (far side) that is inserted into a body while the right side is a proximal side (a near side or a base side) that is manipulated by a technician such as a doctor. For ease of understanding, small components such as first wires 26a and second wires 26b of a braid 26, which are described below, are slightly exaggerated throughout the drawings relative to the dimensions of other components.

The catheter 1 illustrated in FIG. 1 is a tubular medical device having a full length of approximately 1200 mm. The catheter 1 mainly includes a catheter body 10 having flexibility, a distal tip 12 bonded to a distal end portion 11 of the catheter body 10, and a connector 14 fixed to a proximal portion of the catheter body 10.

As illustrated in FIGS. 2 and 3, the catheter body 10 includes an inner layer 24, a braid 26 serving as a reinforcement member, and an outer layer 28, which are radially arranged in this order from the inside.

The inner layer 24 is made of a resin and defines a lumen 18 through which a guide wire or another catheter is inserted. The resin material that the inner layer 24 is made of is not particularly limited, but polytetrafluoroethylene (PTFE) is employed in the embodiment.

A braid 26, which serves as a reinforcement member, surrounds the outer periphery of the inner layer 24. As illustrated in FIGS. 2, 4B, 8B, and 9B, the braid 26 is obtained by weaving first wires 26a and second wires 26b into a net (i.e., into a mesh). In this embodiment, eight first wires 26a and eight second wires 26b, that is, 16 (8+8) wires are alternately woven together. In other words, the first wires 26a are wound in one direction while the second wires 26b are wound in another direction.

Figure 4A:
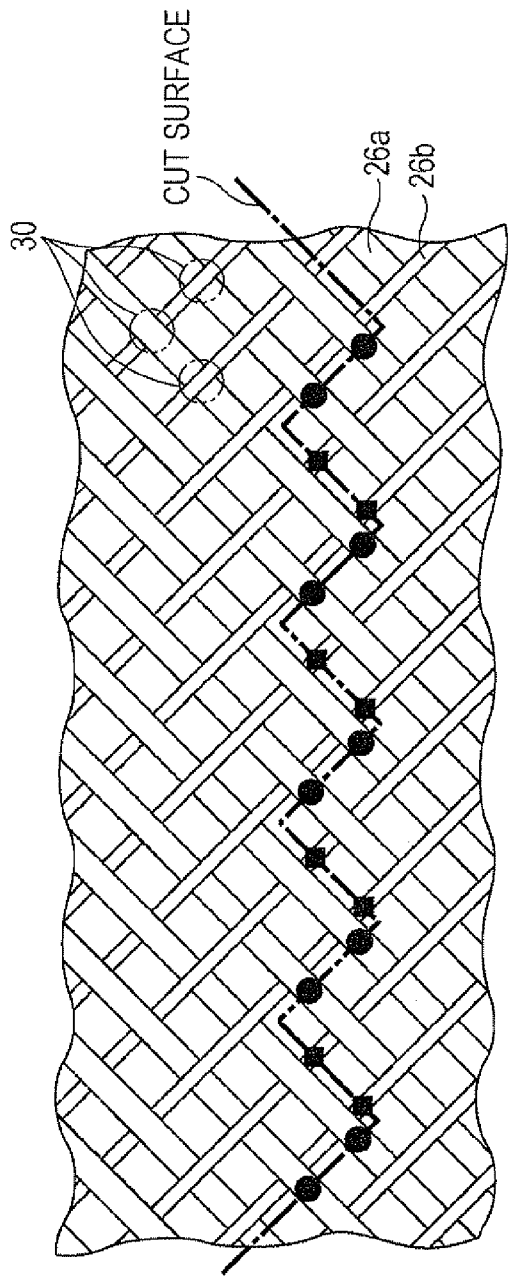
FIG. 4A is a plan view of a distal end portion of a braid before being cut.
Figure 8A:
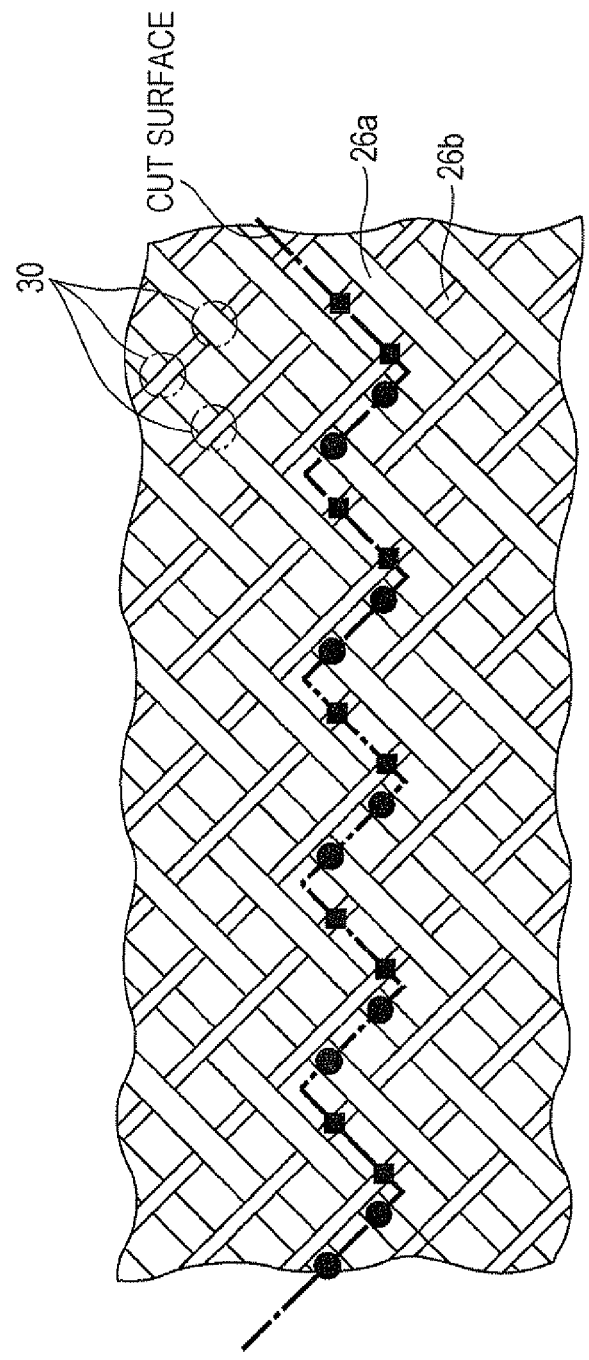
FIGS. 8A and 8B are plan views of a distal end portion of a braid according to an embodiment other than that illustrated in FIGS. 4A and 4B.
Figure 8B:
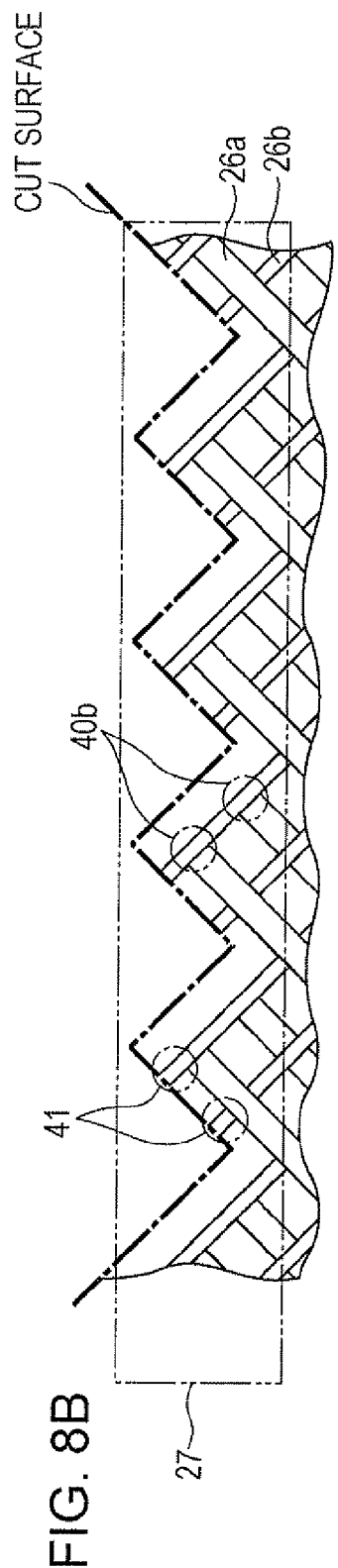

The combination of the first wires 26a and the second wires 26b of the braid 26 is not limited to the above example of 8+8 wires. The combination may be a balanced combination, such as 4+4 wires or 2+2 wires, or an unbalanced combination, such as 4+8 wires or 2+4 wires. The wire width of the first wires 26a and the wire width of the second wires 26b may be the same or the wire width of the first wires 26a may be larger than the wire width of the second wires 26b. In FIGS. 4A, 8B, and 9B, the first wires 26a and the second wires 26b are woven such that the first wires 26a alternately cross over two second wires 26b (every other second wire 26b) and then cross under two second wires 26b. Alternatively, the first wires 26a and the second wires 26b may be woven such that the first wires 26a alternately cross over one second wire 26b and then cross under one second wire 26b.

The first wires 26a and the second wires 26b may be made of the same material or different materials. In this embodiment, the first wires 26a made of a stainless steel (Japanese Industrial Standards (JIS) No. SUS316), having a low melting point, and the second wires 26b made of tungsten, having a high melting point, are used. However, wires may be made of materials other than metals, such as reinforced plastics. In this embodiment, the cross sectional shape of the first wires 26a and the second wires 26b may be circular or rectangular.

The outer layer 28, which is made of a resin, surrounds the outer periphery of the braid 26 and covers the inner layer 24 and the braid 26. The resin material that the outer layer 28 is made of is not particularly limited and may be polyamide, a polyamide-based elastomer, polyester, polyurethane, or the like.

As illustrated in the cross sectional view of FIG. 3, a portion of the catheter body 10 is covered by the outer layer 28, the portion excluding a portion of the catheter body 10 having a length equivalent to the length X of the distal tip 12 from a tip opening 15 of the catheter body 10. The outer layer 28 is made of resin materials having different hardnesses such that the catheter 10 becomes increasingly more flexible from the proximal side toward distal side. As illustrated in FIG. 3, the braid 26 is covered by a resin-made middle layer 29 and the resin-made outer layer 28, but is not limited to this structure. The catheter body 10 may be formed without using the middle layer 29 so that the outer diameter of the catheter body 10 can be reduced. The middle layer 29 may be made of a resin material that is the same as or different from the resin material of the inner layer 24 or the outer layer 28.

In the cross sectional view of FIG. 3, the distal end portion 11 of the catheter body 10 has a uniform inner diameter in the axial direction, but is not limited to this structure. Only the distal end portion 11 of the catheter body 10 may have a tapered shape such that the inner diameter is widened toward the proximal end of the catheter body 10.

The distal tip 12, which is made of a resin, is attached to a distal end of the catheter body 10. The distal tip 12 is a cylindrical member having the tip opening 15. The resin that the distal tip 12 is made of is not particularly limited and may be polyurethane, a polyurethane-based elastomer, or the like. The distal tip 12 may contain a radiopaque powder. For example, if the distal tip 12 contains approximately 65 wt % to approximately 90 wt % of a radiopaque powder (tungsten powder, for example), a technician such as a doctor can accurately recognize the position of the catheter during coronary artery imaging.

Subsequently, the distal end portion 27 of the braid 26 is described.

Figure 4B:
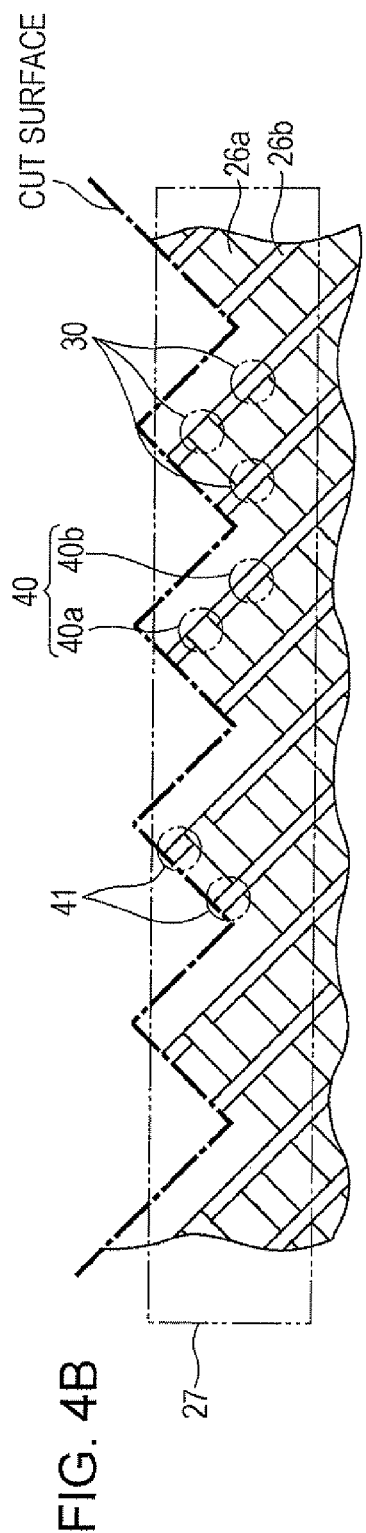
FIG. 4B is a plan view of the distal end portion of the braid after being cut.

As illustrated in FIG. 4B, the distal end portion 27 of the braid 26 has distal end portions 40 of the first wires 26a, which join to the second wires 26b by winding themselves around the second wires at or around intersection points 30 at which the first wires 26a and the second wires 26b cross one another, and distal end portions 41 of the second wires 26b, which do not join to the first wires 26a.

The distal end portions 40 of the first wires 26a are divided into distal end portions 40a, extending from an upper side to a lower side (or toward the catheter body 10), and distal end portions 40b, extending from the lower side to the upper side (or away from the catheter body 10).

Figure 5A:
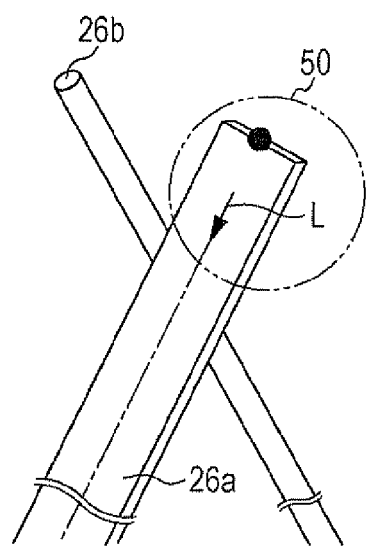
FIG. 5A illustrates a distal end portion of a first wire and a distal end portion of a second wire.
Figure 5B:
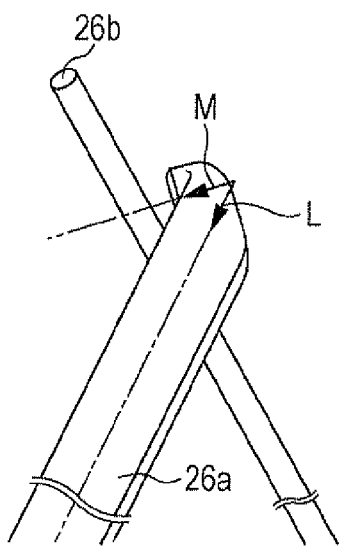
FIG. 5B illustrates the distal end portion of the first wire that is moving in the axial direction L of the first wire and in a direction M that crosses the axial direction L.

Now, a method of manufacturing the distal end portions 40a of the first wires 26a will be described. As illustrated in FIGS. 4A and 5A, when the positions of the first wires 26a indicated by filled circles are irradiated with a laser beam, a fusion portion 50 of each first wire 26a near the position that is irradiated with the laser beam is fused with an energy of the laser beam. As illustrated in FIG. 5B, the fused fusion portion 50 solidifies while moving in the axial direction L of the first wire 26a and in a direction M that crosses the axial direction L. Consequently, as illustrated in FIG. 5C, the distal end portion 40a of the first wire 26a winds itself around the side surface of the second wire 26b from an upper side to a lower side, thereby forming a joint 100 with which the first wire 26a and the second wire 26b are joined together.

The joint 100 includes a joint portion 110 positioned at the intersection point 30 at which the first wire 26a and the second wire 26b cross each other, a joint portion 120 positioned beyond the intersection point 30 in the width direction N of the first wire 26a, and a joint portion 130 positioned beyond the intersection point 30 in the width direction N' of the second wire 26b.

By thus wrapping the distal end portion 40a of the first wire 26a around the side surface of the second wire 26b, the first wire 26a and the second wire 26b can be joined together via the joint 100 without using another member such as a clip or an adhesive. Even when the first wire 26a and the second wire 26b have small thicknesses, joint strength between the first wire 26a and the second wire 26b can be flexibly adjusted by increasing the area of the joint portion 120 positioned beyond the intersection point 30.

Figure 5C:
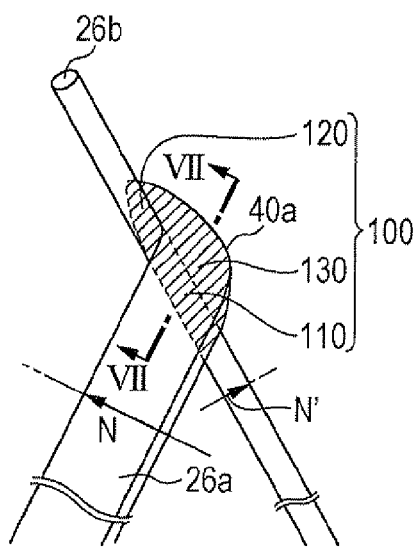
FIG. 5C illustrates a joint at which the distal end portion of the first wire covers a side surface of the second wire so as to extend from an upper side toward a lower side.

As illustrated in FIGS. 5B and 5C, the distal end portion 40a of the first wire 26a obtained after the fusion portion 50 is fused and solidifies extends in the axial direction L of the first wire 26a and in a direction M that crosses the axial direction L. The axial direction L of the first wire 26a may form an angle with the direction M that crosses the axial direction L, for example, an acute angle. Therefore, even if an external force would be exerted on the braid 26 when the catheter body 10 is inserted into a blood vessel and comes into contact with the inner wall of the blood vessel, the joint 100 could resist not only an external force exerted in the axial direction L of the first wire 26a but also an external force exerted in the direction M deviated from the axial direction L. Thus, a catheter 1 in which the first wires 26a and the second wires 26b are joined together with high joint strength can be produced.

Figure 6A:
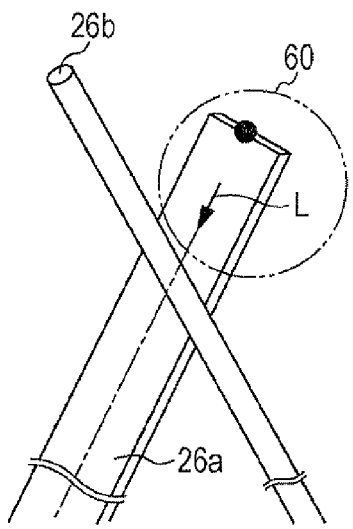
FIG. 6A illustrates a distal end portion of a first wire and a distal end portion of a second wire.
Figure 6B:
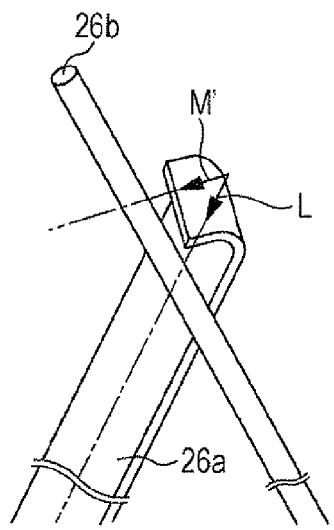
FIG. 6B illustrates the distal end portion of the first wire that is moving in the axial direction L of the first wire and in a direction M' that crosses the axial direction L.

Likewise, a method of manufacturing the distal end portions 40b of the first wires 26a will be described. As illustrated in FIG. 6A, when the position of the first wire 26a indicated by a filled circle is irradiated with a laser beam, a fusion portion 60 of the first wire 26a near the position that is irradiated with a laser beam is fused with an energy of the laser beam. As illustrated in FIG. 6B, the fused fusion portion 60 solidifies while moving in the axial direction L of the first wire 26a and in a direction M' that crosses the axial direction L. Consequently, as illustrated in FIG. 6C, the distal end portion 40b of the first wire 26a winds itself around the side surface of the second wire 26b from a lower side to an upper side, thereby forming a joint 200 with which the first wire 26a and the second wire 26b are joined together.

The joint 200 includes a joint portion 210 positioned at the intersection point 30 at which the first wire 26a and the second wire 26b cross each other, a joint portion 220 positioned beyond the intersection point 30 in the width direction N of the first wire 26a, and a joint portion 230 positioned beyond the intersection point 30 in the width direction N' of the second wire 26b.

By thus wrapping the distal end portion 40b of the first wire 26a around the side surface of the second wire 26b, the first wire 26a and the second wire 26b can be joined together via the joint 200 without using another member such as a clip or an adhesive. Even when the first wire 26a and the second wire 26b have small thicknesses, joint strength between the first wire 26a and the second wire 26b can be flexibly adjusted by increasing the area of the joint portion 220 positioned beyond the intersection point 30.

Figure 6C:
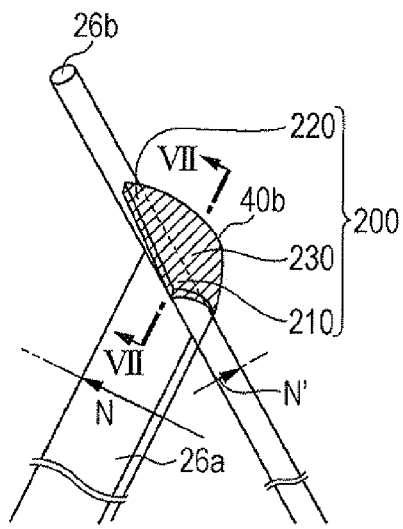
FIG. 6C illustrates a joint at which the distal end portion of the first wire covers a side surface of the second wire so as to extend from a lower side toward an upper side.

As illustrated in FIGS. 6B and 6C, the distal end portion 40b of the first wire 26a obtained after the fusion portion 60 is fused and solidifies extends in the axial direction L of the first wire 26a and in a direction M' that crosses the axial direction L. Therefore, even if an external force would be exerted on the braid 26 when the catheter body 10 is inserted into a blood vessel and comes into contact with the inner wall of the blood vessel, the joint 200 could resist not only an external force exerted in the axial direction L of the first wire 26a but also an external force exerted in the direction M' deviated from the axial direction L. Thus, a catheter 1 in which the first wires 26a and the second wires 26b are joined together with high joint strength can be produced.

The directions L, M, and M' in which the fused fusion portions 50 and 60 move and the distance that the fused fusion portions 50 and 60 move can be controlled by adjusting various conditions, such as the position of the first wires 26a to which a laser beam is irradiated, the intensity of a laser beam that is emitted, the thickness of the first wires 26a, or an irradiation atmosphere. Thus, the length of the fusion portions 50 may be the same or different from the length of the fusion portions 60. The direction M in which the fusion portions 50 move while being fused may be the same as or different from the direction M' in which the fusion portions 60 move while being fused.

As described above, the length of the joint portions 120 and 220 positioned beyond the intersection point 30 can be flexibly changed. Thus, by increasing the area of the joint portions 120 and 220, even the first wires 26a and the second wires 26b of the braid 26 having small thicknesses can be joined together at high joint strength.

By forming the joints 100 and 200 according to the embodiment, the first wires 26a and the second wires 26b can be joined together without using another member such as a clip or an adhesive. In addition, the size of the braid 26 (and thus the outer diameter of the catheter body 10) can be reduced while the first wires 26a and the second wires 26b are joined together with high joint strength.

Although the joints 100 and 200 have been described as having such a shape that the distal end portions 40 of the first wires 26a cover the side surfaces of the second wires 26b, the joints are not limited to this configuration. For example, the joints 100 and 200 may have such a shape that a distal end portion 40 of each first wire 26a covers the side surface and the upper surface (or lower surface) of the corresponding second wire 26b. In the case where the distal end portion 40 of the first wire 26a covers the upper surface (or the lower surface) of the second wire 26b, however, the thickness of the joint 100 or 200 is increased, accordingly. Therefore, it is preferable that the distal end portion 40 of the first wire 26a cover only the side surface of the corresponding second wire 26b in view of the size reduction of the braid 26.

Figure 7:
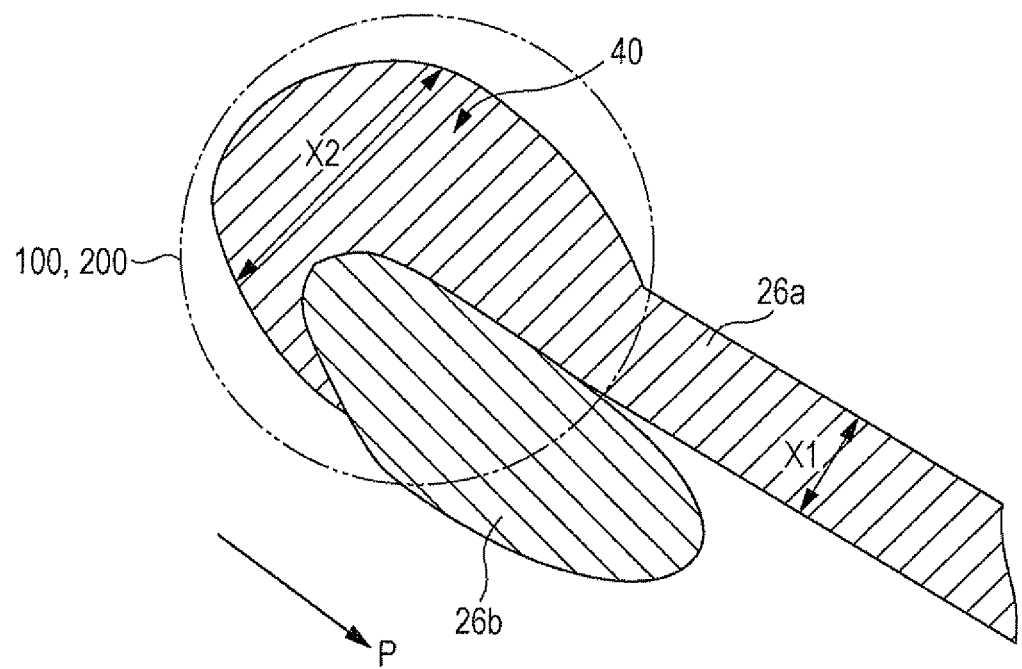
FIG. 7 is a cross-sectional view of the first wire and the second wire taken along the line VII-VII of FIGS. 5C and 6C.

FIG. 7 is a cross sectional view of the first wire 26a and the second wire 26b taken along the line VII-VII of FIGS. 5C and 6C. When the thickness of a main portion of the first wire 26a is denoted by X1 and the thickness of the distal end portion 40 of the first wire 26a is denoted by X2, the relationship X2>X1 is satisfied. This is because the distal end portion 40 of the first wires 26a bulges as a result of the fusion and solidification of the fusion portion 50 or 60.

Since the fusion portion 50 or 60 of the first wire 26a is added to the distal end portion 40, the mass of the first wire 26a at the joint 100 or 200 is increased, thereby increasing the normal reaction. Consequently, the second wires 26b can be prevented from being detached from the first wires 26a when an external force is exerted on the second wires 26b in the direction P (in other words, when the second wires 26b are pulled to a side on which the joints 100 or 200 are not formed) because the frictional resistance between the first wires 26a and the second wires 26b is large at the joints 100 or 200. Therefore, even when the first wires 26a and the second wires 26b have small thicknesses, the first wires 26a and the second wires 26b can be joined together with high joint strength by only increasing the proportion of the fusion portions 50 and 60 so as to increase the thickness of the first wires 26a at the joints 100 and 200. Thus, the size of the catheter body 10 can be reduced while the first wires 26a and the second wires 26b are joined together with high joint strength.

In FIG. 4B, the distal end portions 40 of the first wires 26a include the distal end portions 40a and the distal end portions 40b, which are alternately arranged, and thus the second wires 26b are prevented from moving vertically. However, as illustrated in FIG. 8B, the distal end portions 40 of the first wires 26a may include only the distal end portions 40b. Even in this case, the first wires 26a and the second wires 26b can be joined together with high joint strength by adjusting conditions such as the thickness X2 of the distal end portions 40b of the first wires 26a or the length of the joints 220 formed at positions beyond the intersection points 30.

In FIGS. 4B and 8B, the first wires 26a and the second wires 26b are cut such that the distal end portion 27 of the braid 26 has recesses and protrusions (valleys and peaks). However, the present invention is also applicable to the case where the distal end portion 27 of the braid 26 is cut straight as illustrated in FIG. 93. In FIG. 9B, as in the case of FIG. 4B, the distal end portions 40a and the distal end portions 40b of the first wire 26a are alternately arranged. Thus, the distal end portions 40a and the distal end portions 40b can be joined together such that the second wires 26b can be prevented from moving vertically.

Now, a description is given on a method of manufacturing the catheter body 10 including the braid 26 in which the first wires 26a and the second wires 26b are joined together via the joints 100 and 200. Although the description is given referring to FIGS. 4A and 4B, methods of manufacturing catheter bodies including the braids 26 according to other embodiments illustrated in FIGS. 8A, 8B, 9A, and 9B are basically the same, and thus are not described here.

First, the inner layer 24 and the braid 26 are formed on a core. In this state, a laser beam is emitted to the positions of the first wires 26a of the braid 26 indicated by filled circles and the positions of the second wires 26b of the braid 26 indicated by filled squares, so that unnecessary portions of the first wires 26a and the second wires 26b that extend toward the distal end are cut off. Thus, the fusion portions 50 and 60, which are to serve as the distal end portions 40 of the first wires 26a, and the distal end portions 41 of the second wires 26b are formed.

When a laser beam is emitted to the fusion portions 50 and 60 of the first wires 26a again, the fused fusion portions 50 and 60 solidify while moving in the axial direction L of the first wires 26a and in the direction M or M' that crosses the axial direction L and become the distal end portions 40 of the first wires 26a. Consequently, the joints 100 and 200 in which the distal end portions 40 of the first wires 26a wind themselves around the side surfaces of the second wires 26b are formed. Here, the second wires 26b are not deformed even when the fused fusion portions 50 and 60 are wrapped around the side surfaces of the second wires 26b because the melting point of the first wires 26a is lower than the melting point of the second wires 26b. Therefore, joining the first wires 26a and the second wires 26b via the joints 100 and 200 does not lower the durability of the braid 26.

The positions to which a laser beam is emitted are not limited to the positions indicated by the filled circles and the filled squares of FIG. 4A and may be appropriately changed to positions deviated from the intersection points 30 at which the first wires 26a and the second wires 26b cross one another. The joints 100 may be formed after cutting the first wires 26a and the second wires 26b in the above embodiment, but the invention is not limited to this procedure. The first wires 26a may be cut at the same time as the joints 100 and 200 are formed by adjusting the intensity of a laser beam used for irradiation.

The laser beam used to cut the first wires 26a and the second wires 26b or to form the joints 100 and 200 is not particularly limited. In this embodiment, an yttrium aluminum garnet (YAG) pulsed laser is used.

After the first wires 26a and the second wires 26b are joined together via the joints 100 and 200, a resin-made tube, which is to serve as the outer layer 28, is covered around the outer periphery of the braid 26 and heated to a predetermined temperature so as to melt and adhere to the braid 26. The outer layer 28 is caused to adhere to a portion of the braid 26 excluding a portion of the braid 26 having a length equivalent to the length X of the distal end tip 12, as shown in FIG. 3, for example.

Then, a resin-made tube, which is to serve as the distal tip 12, is covered around the distal end portion 27 of the braid 26 and heated to a predetermined temperature so as to melt and adhere to the distal end portion 27. Thus, the distal tip 12 is caused to adhere to the distal end portion 11 of the catheter body 10.

Thereafter, when the core is removed, a catheter 1 including the distal end portion 11 of the catheter body 10 and the distal tip 12 can be obtained.

In this embodiment, the distal end portions 41 of the second wires 26b are not joined to the first wires 26a, but the invention is not limited to this configuration. If the joint strength between the first wires 26a and the second wires 26b at the joints 100 and 200 is insufficient, the distal end portions 41 of the second wires 26b may be wrapped around the side surfaces of the first wires 26a by emitting a laser beam to the distal end portions 41 again.

As described above, in this embodiment, the first wires 26a and the second wires 26b can be joined together by wrapping the distal end portions 40 of the first wires 26a around the side surfaces of the second wires 26b. Each joint 100 or 200 includes a joint portion 110 or 210 positioned at the corresponding intersection point 30, a joint portion 120 or 220 positioned beyond the intersection point 30 in the width direction N of the first wire 26a, and a joint portion 130 or 230 positioned beyond the intersection point 30 in the width direction N' of the second wire 26b. Thus, even when the first wires 26a and the second wires 26b have small thicknesses for size reduction of the braid 26, the first wires 26a and the second wires 26b can be joined together with high joint strength by increasing the area of the joint portions 120 and 220 or the thickness of the joint portions 130 and 230.

What is claimed is:

1. A catheter comprising:
   an inner layer made of a resin;
   a braid surrounding an outer periphery of the inner layer, the braid including a first wire and a second wire; and
   an outer layer surrounding an outer periphery of the braid, the outer layer being made of a resin,
   wherein:
   the first wire and the second wire are joined together via a joint at which a distal end portion of the first wire is wrapped around a side surface of the second wire, and
   a thickness in a radial direction of the catheter of a portion of the first wire at the joint is larger than a thickness in the radial direction of the catheter of a portion of the first wire other than the portion of the first wire at the joint.

2. The catheter according to claim 1, wherein the joint is positioned beyond the first wire in a width direction of the first wire.

3. The catheter according to claim 1, wherein the distal end portion of the first wire extends in an axial direction of the first wire and in a direction that crosses the axial direction.

4. The catheter according to claim 2, wherein the distal end portion of the first wire extends in an axial direction of the first wire and in a direction that crosses the axial direction.

5. A catheter comprising:
   an inner layer;
   a braid surrounding an outer periphery of the inner layer, the braid including a plurality of first wires and a plurality of second wires; and
   an outer layer surrounding an outer periphery of the braid, wherein;

the plurality of first wires and the plurality of second wires are woven together in a mesh structure, an end portion of each of the plurality of first wires is partially wrapped around an outer surface of a corresponding one of the plurality of second wires to form a joint, the end portion of each of the plurality of first wires extending in a direction that is different from an axial direction of each of the plurality of first wires, and for each of the plurality of first wires, a thickness in a radial direction of the catheter of a portion of the first wire at the joint is larger than a thickness in the radial direction of the catheter of a portion of the first wire other than the portion of the first wire at the joint.

6. The catheter according to claim 5, wherein an angle formed by the direction in which the end portion extends and the axial direction of each of the plurality of first wires is an acute angle.

7. The catheter according to claim 5, wherein an end portion of each of the second wires is not joined to the plurality of first wires.

8. The catheter according to claim 5, wherein each of the joints includes a first joint portion positioned at an intersection point at which one of the plurality of first wires and one of the plurality of second wires cross each other, a second joint portion positioned beyond the intersection point in a width direction of the one of the plurality of first wires, and a third joint portion positioned beyond the intersection point in a width direction of the one of the plurality of second wires.

9. The catheter according to claim 5, wherein the end portion of each of the plurality of first wires is partially wrapped around at least a side surface of the corresponding one of the plurality of second wires.

10. The catheter according to claim 5, wherein the end portion of each of the plurality of first wires is partially wrapped around the outer surface of the corresponding one of the plurality of second wires without using another member.

* * * * *